United States Patent [19]

Nishimura et al.

[11] Patent Number: 5,410,069

[45] Date of Patent: Apr. 25, 1995

[54] POLYMERIZABLE COMPOUND, PROCESS FOR PRODUCING SAME AND SETTING COMPOSITION CONTAINING POLYMERIZABLE COMPOUND

[75] Inventors: Shin Nishimura, Katsuta; Yoshinori Kawai, Hitachi; Satoru Amou, Hitachi; Akira Nagai, Hitachi; Masahiro Suzuki, Iwaki; Akio Takahashi, Hitachiota; Akio Mukoh, Mito, all of Japan

[73] Assignee: Hitachi, Ltd., Tokyo, Japan

[21] Appl. No.: 986,758

[22] Filed: Dec. 8, 1992

[30] Foreign Application Priority Data

Dec. 10, 1991 [JP] Japan .................. 3-325531

[51] Int. Cl.$^6$ ........................ C07D 207/444
[52] U.S. Cl. .................... 548/547; 548/548; 548/549
[58] Field of Search ............ 548/548, 549, 547

[56] References Cited

U.S. PATENT DOCUMENTS

| | | | |
|---|---|---|---|
| 4,593,083 | 6/1986 | Stenszenberger | 526/262 |
| 4,777,237 | 10/1988 | Dien et al. | 528/322 |

FOREIGN PATENT DOCUMENTS

| | | |
|---|---|---|
| 0051687 | 5/1982 | European Pat. Off. |
| 0077840 | 5/1983 | European Pat. Off. |
| 0176328 | 9/1984 | European Pat. Off. |
| 0208634 | 1/1987 | European Pat. Off. |
| 0446718 | 9/1991 | European Pat. Off. |
| 2720311 | 11/1978 | Germany |
| 2934578 | 3/1980 | Germany |
| 3012179 | 10/1980 | Germany |
| 58-132010 | 8/1983 | Japan |
| 63-56548 | 3/1988 | Japan |

*Primary Examiner*—Joseph L. Schofer
*Assistant Examiner*—Wu C. Cheng
*Attorney, Agent, or Firm*—Antonelli, Terry, Stout & Kraus

[57] ABSTRACT

A polymerzable compound represented by the general formula (1) $X-R_1-Y$ where X is un unsaturated imide group having substituents $R_2$ and $R_3$, or an itacon imide group where $R_2$ and $R_3$ are selected from the group consisting of hydrogen, a lower alkyl group and an aromatic group having a substituent p which is hydrogen, a lower alkyl group, or an alkoxy group, and Y is a styryl group, and $R_1$ is a divalent organic group.

The polymerizable compounds is excellent in formability, and find a wide variety of applications because they have functional groups different in reactivity from each other and hence allow the curing conditions to control. The cured polymers are excellent in thermal durability, mechanical properties and electrical properties, making it possible to achieve higher performance, higher reliability, highly compact and lower weight of electric apparatuses and electronic parts.

33 Claims, No Drawings

POLYMERIZABLE COMPOUND, PROCESS FOR PRODUCING SAME AND SETTING COMPOSITION CONTAINING POLYMERIZABLE COMPOUND

BACKGROUND OF THE INVENTION

1. Field of the Invention

The present invention relates to a novel polymerizable compound having functional groups different in reactivity, a process for producing the same, and a polymer obtained from a composition containing the polymerizable compound. Especially, the present invention achieves effectively enhancement in characteristics of such as formability, heat-resistance, mechanical properties and electric properties of the polymers, rendering the polymers useful as insulating materials for electric apparatuses and protective coating materials.

2. Description of Related Art

Conventional thermosetting resin compositions having excellent formability, heat-resistance and mechanical properties to be used for insulating layers in multilayer printed circuit boards contain as components polymers having three dimensionally cross-linkable functional groups in side chains. For example, Japanese Patent KOKAI (Laid-open) No. Sho 63-56548 discloses poly(p-hydroxystyrene) derivatives having alkenyl or alkenoyl groups in side chains. In order to produce such polymers having the functional groups in side chains, a process where introduction of the functional groups into the side chains can be made by reacting the hydroxyl groups of the poly(p-hydroxystyrene) with alkenyl chloride or alkenoyl chloride is known. These polymer precursors to be used as starting materials for production of the setting polymers are considered to have hydroxyl, carboxyl, amino groups or the like introduced in side chains. Polymerization of these addition-polymerizable monomers having such functional groups requires protection of the functional groups as reported in Proceedings, KOBUNSHI GAKKAI, Vol. 39, No. 6, pp.1730-1732.

Compounds having functional groups different in reactivity are known as Japanese Patent Publication, No. Hei 3-43287 discloses multi-functional compounds which are produced by introducing a maleimide derivative into a styrene derivative residue, one of which, N-(p-vinylphenyl) maleimide is clarified for its polymerization reactivity. It is known that when an anionic initiator, alkali metal t-butoxyde is used, the maleimide groups polymerize, while a cationic initiator, $BF_3O(CH_2CH_3)_2$ is used, the vinyl groups polymerize as disclosed in Proceedings, KOBUNSHI GAKKAI, Vol. 39, No. 2, p. 266.

However, the introduction of reactive functional groups into side chains limits the processes therefor to such that ester functional groups such as acrylate, methacrylate, and the like capable of being readily introduced are introduced by using chlorides, or that amino groups are maleimidized. For this reason, in order to obtain cured products having a combination of necessitate heat resistance, mechanical characteristics and formability, one resin has been needed to be blended with other ones for supplementing some properties, of which the resin alone is devoid. This causes a problem of generation of crackes and the like due to phase separation, which leads to a difficulty in determination of curing conditions for production of homogeneous cured resin products.

SUMMARY OF THE INVENTION

It is an object of the present invention to provide a novel polymerizable compound having functional groups different in reactivity from each other, and being capable of producing readily a homogeneous cured resin product having a combination of heat resistance, mechanical characteristics and formability, and a process for producing the same, and a composition containing the polymerizable compound, and a polymer therefrom.

Broadly, the present invention relates to the followings:

1. A polymerzable compound represented by the following general formula (1):

where X is an unsaturated imide group having substituents $R_2$ and $R_3$, or an itacon imide group where $R_2$ and $R_3$ are the same or different from each other and selected from the group consisting of hydrogen, a lower alkyl group, halogen and an aromatic group having a substituent p which is hydrogen, a lower alkyl group, or an alkoxy group, and R is a divalent organic group, and Y is a styryl group represented by the general formula:

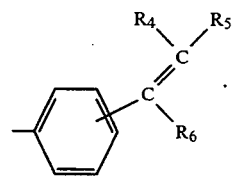

where $R_4$, $R_5$ and $R_6$ are the same or different from one another and selected from the group consisting of $CH_3$, $C_2H_5$, $C_3H_7$, F and $CF_3$.

2. A polymerzable compound represented by the following general formula (2):

where X is a group having at least one N-substituted unsaturated imide group, Y is different from X and an anionically polymerizable or cationically polymerizable group, $R_1$ is an aromatic bond having a bonding group $—R_0—$ where $R_0$ is a divalent organic group having 1 to 20 carbon atoms.

3. A polymerzable compound represented by the following general formula (3):

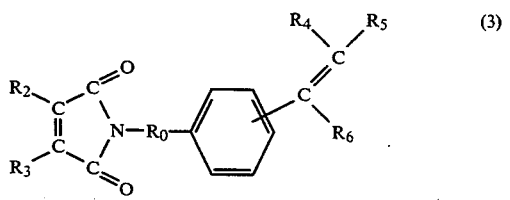

where $R_0$ is a divalent organic group having 1 to 20 carbons, $R_2$ and $R_3$ are the same or different from each other and selected from the group consisting of hydrogen, a lower alkyl group, halogen and an aromatic group having a substituent p which is hydrogen, a lower alkyl group, or an alkoxy group, $R_4$, $R_5$ and $R_6$ are the same or different from one another and selected from the group consisting of $CH_3$, $C_2H_5$, F and $CF_3$.

In another aspect, the present invention relates to a setting composition comprising a polymerizable compound represented by the general formula (1) as described above and an anionic polymerization initiator or a cationic polymerization initiator.

In still another aspect, the present invention relates to a polymer having cationically polymerizable groups or anionically polymerizable groups produced by reacting the aforementioned setting composition.

In still another aspect, the present invention relates to a setting composition characterized by comprising a polymer as defined above with an addition of a cationic polymerization initiator and an anionic polymerization initiator separately. In still another aspect, the present invention relates to a process for producing a polymer having a repeating unit represented by the following general formula (12):

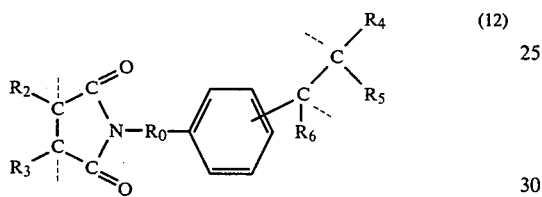
(12)

where $R_0$ and $R_2$ to $R_6$ are as defined above, by setting said setting composition.

In the present invention, the polymerizable compounds represented by the aforementioned general formula (1):

$X-R_1-Y$ (1)

where X is an unsaturated imide group having substituents $R_2$ and $R_3$, or an itacon imide group where $R_2$ and $R_3$ are the same or different from each other and selected from the group consisting of hydrogen, a lower alkyl group, halogen and an aromatic group having a substituent p which is hydrogen, a lower alkyl group, or an alkoxy group, and R is a divalent organic group, and Y is a styryl group represented by the general formula:

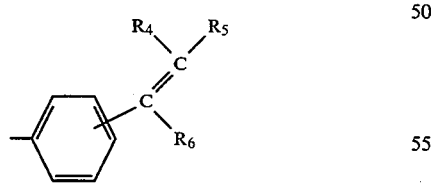

where $R_4$, $R_5$ and $R_6$ are the same or different from one another and selected from the group consisting of $CH_3$, $C_2H_5$, $C_3H_7$, F and $CF_3$, include, or example,

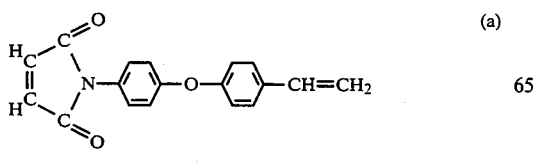
(a)

-continued

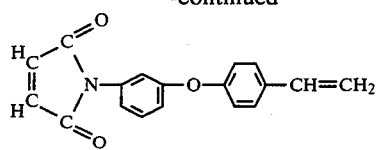
(b)

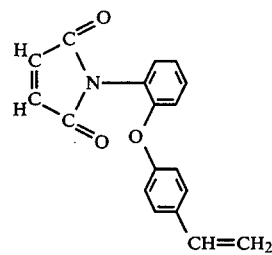
(c)

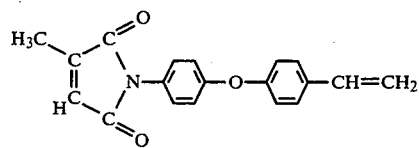
(d)

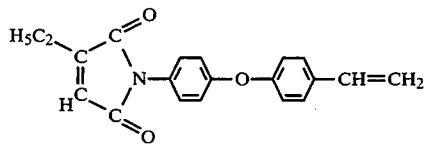
(e)

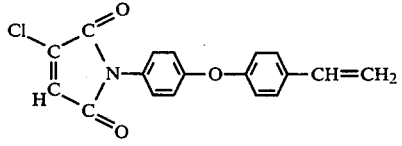
(f)

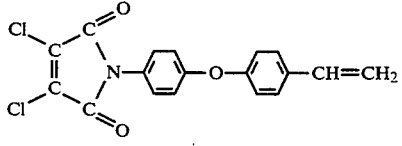
(g)

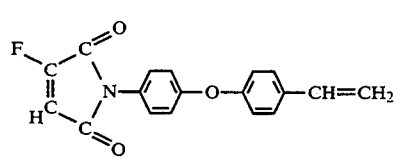
(h)

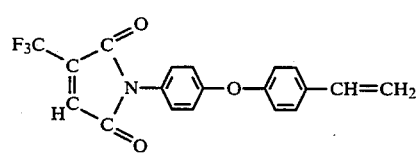
(i)

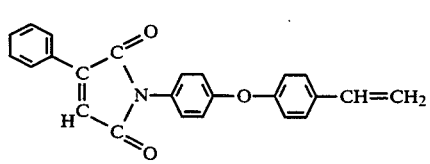
(j)

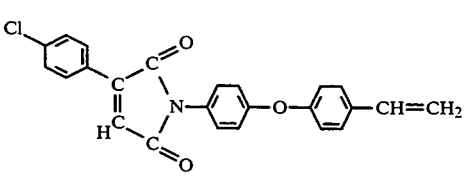
(k)

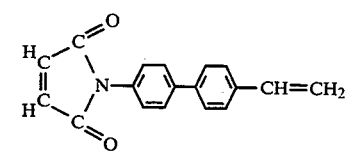 (l)
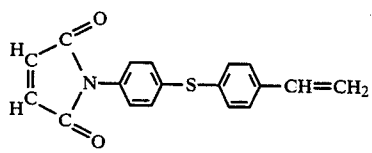 (m)
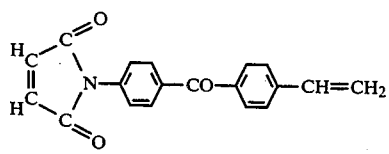 (n)
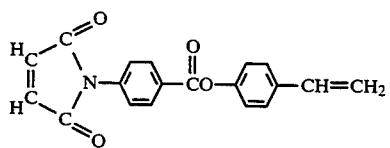 (o)
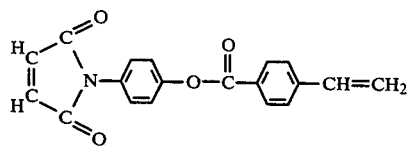 (p)
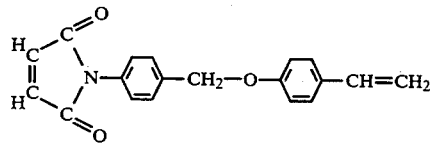 (q)
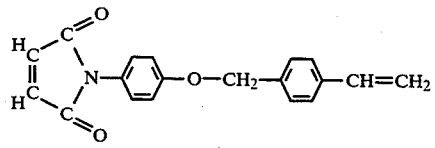 (r)
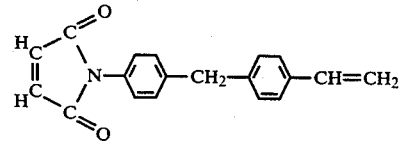 (s)
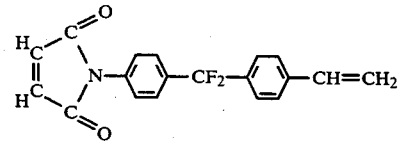 (t)
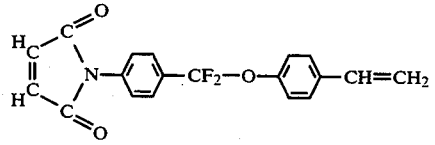 (u)
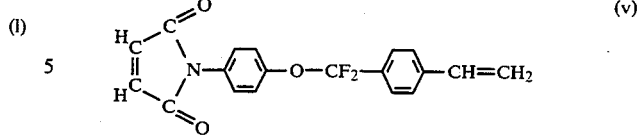 (v)
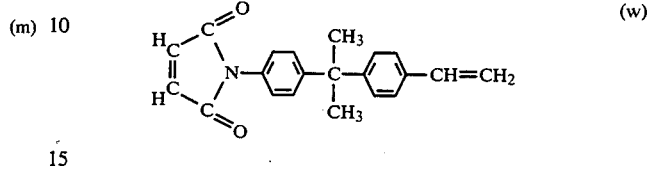 (w)
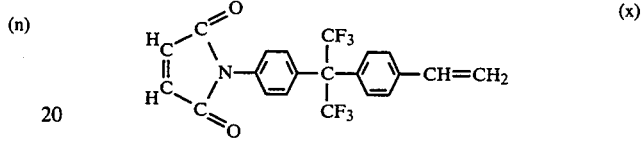 (x)
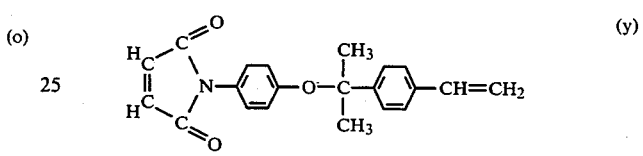 (y)
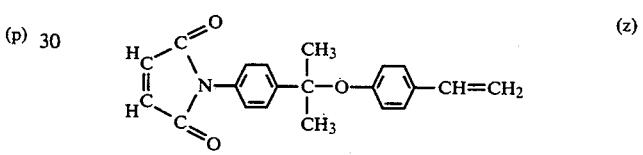 (z)
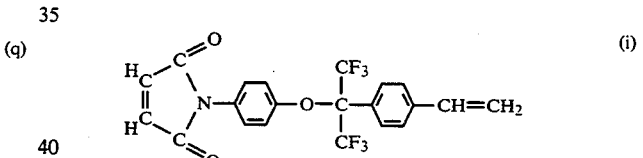 (i)
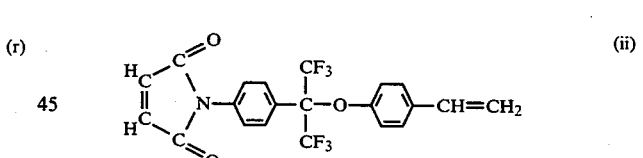 (ii)
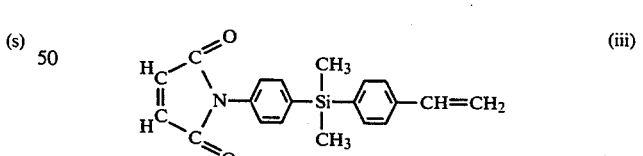 (iii)
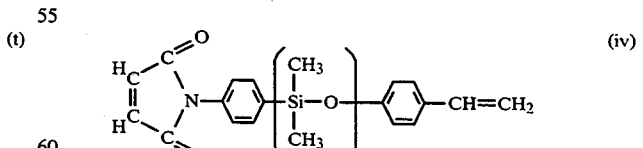 (iv)
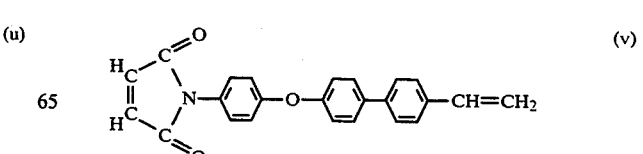 (v)

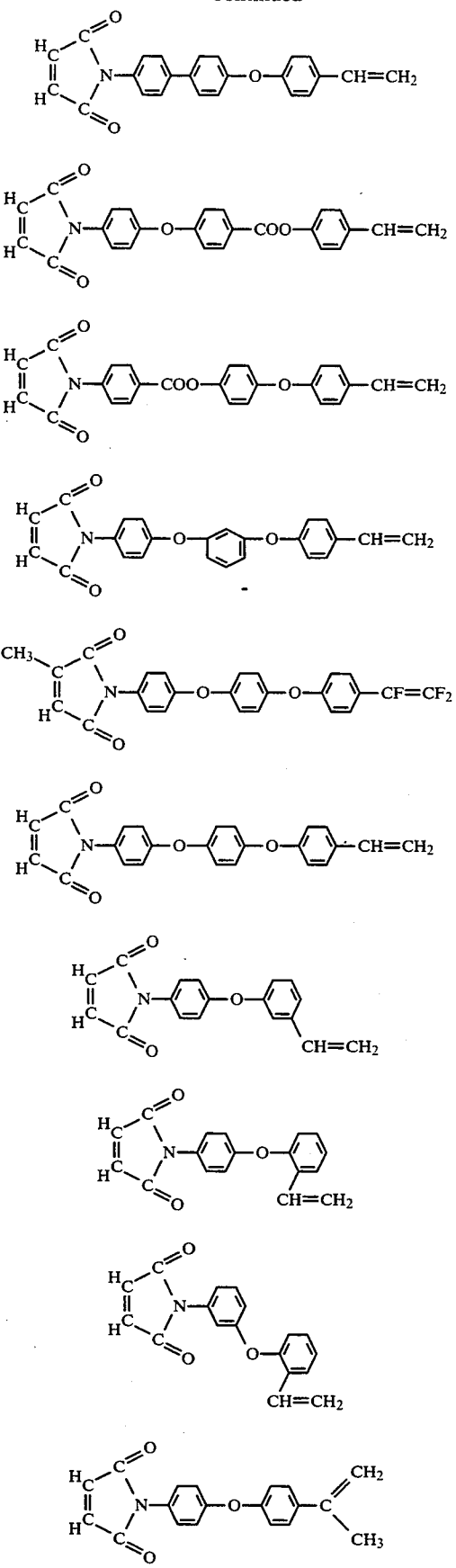
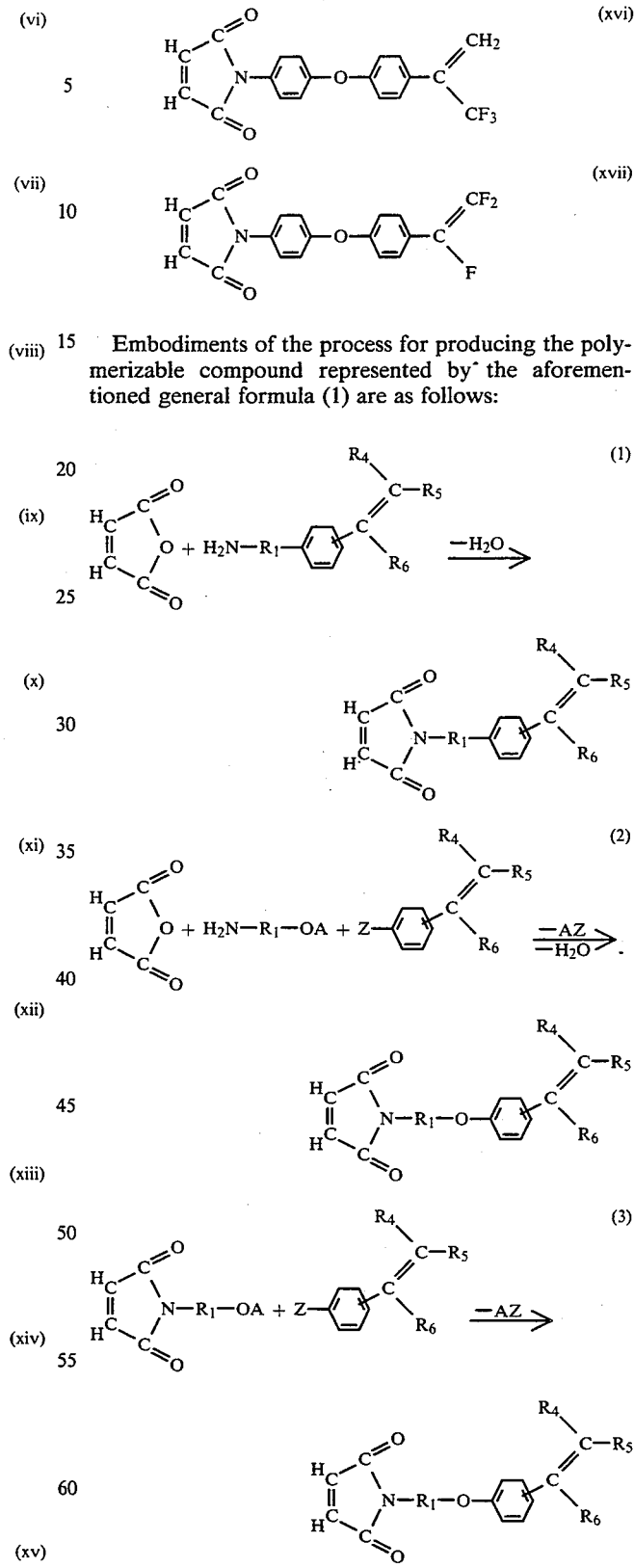
Embodiments of the process for producing the polymerizable compound represented by the aforementioned general formula (1) are as follows:
where X, R₁ and Y are as defined above.
Functional groups which are polymerizable by anionic polymerization, but not by cationic polymerization include vinyl derivatives such as α-nitrovinyl, α- cyanovinyl and α-vinylester groups, and maleimide derivatives such as maleimide, α-phenylmaleimide and α-methymaleimide groups.

Functional groups which are polymerizable by cationic polymerization, but not by anionic polymerization include propylene residue, vinylether residue and the like.

Functional groups which are active both in anionic polymerization and cationic polymerization include styrene derivatives such as styryl group and α-methylstyryl, and butadiene derivatives. These functional groups may be used in the form of a compound having an optional combination of the functional groups by selecting a polymerization initiator in the present invention. For example, in the case of a combination of the styryl groups and the maleimide groups, only the maleimide groups can be polymerized by using an anionic initiator, alkali metal t-butoxide, while only the vinyl groups of the styrene can be polymerized by using a cationic initiator, $BF_3$. In the case of a combination of the α-cyanovinyl groups and the styryl groups, only the α-cyanovinyl groups can be polymerized by using an anionic initiator, alkali metal t-butoxide, while only the vinyl groups of the styrene can be polymerized by using a cationic initiator, $BF_3$. In the case of a combination of the α-cyanovinyl groups and the styryl groups, only the α-cyanovinyl groups can be polymerized by using an anionic initiator, alkali metal t-butoxide, while only the vinyl groups of the styrene can be polymerized by using a cationic initiator, $BF_3$. In the case of a combination of the vinylether residues and the styryl groups, only the vinyl groups of the styrene can be polymerized by using an anionic initiator, alkyl lithium compound, while only the vinylether residues can be polymerized by using a cationic initiator, $BF_3$. The combination of the maleimide groups and the styryl groups is most preferred from the standpoints of thermal resistance, reactivity and formability.

The divalent organic groups represented by the R in the general formula to be used include organic groups such as ether, carbonyl, ester, phenylene, biphenylene, methylene, 1,2-ethylene, 2,2'-propylene, 2,2'-diphenylenepropane, bisphenol A, bisphenol F, amide, imide, surphone, and siloxy groups. Any combination of these organic groups may be optionally used. Such organic groups as having no influence on any one of monomers and functional groups are preferred. The organic groups can be appropriately selected depending upon the monomer's reactivity, polymeric setting properties, and mechanical and electrical properties to be desired for the cured products.

The cured products can be obtained by filling the present setting polymer in a metallic mold at a temperature in the range of rendering the polymer molten, and increasing the temperature to a predetermined polymerization temperature or higher to proceed the cross linking reaction. In such case, an addition of a radical polymerization initiator such as peroxides and the like may be made to allow the polymerization temperature to shift into a lower range as well as to reduce the reaction time.

The radical polymerization initiators include, for example, benzoyl peroxide, p-chlorobenzoyl peroxide, 2,4-dichlorobenzoyl peroxide, lauroyl peroxide, dicumyl peroxide, acetyl peroxide, methylethylketone peroxide, cycrohexanone peroxide, bis(1-hydroxycycrohexyl peroxide, 2,5-dimethylhexane-2,5-dihydroxyl peroxide, t-butyl perbenzoate, 2,5-dimethyl-2,5-(t-butylperoxy)hexane, 2,5-dimethyl-2,5-(t-butylperoxy)hexine-3, 2,5-dimethylphoxyl-2,5-di(peroxybenzoate), cumene hydroperoxide, t-butyl hydroperoxide, t-butyl peroxybenzoate, t-butyl peroxyacetate t-butyl peroxyoctate, t-butyl peroxyisobutylate, dibenzyl peroxide and di-t-butyl peroxyphthalate. These are used alone or in combination of two or more thereof. The amount of the polymerization initiators to be incorporated is 0.01 to 5 % by weight, most preferably 0.1 to 3 parts by weight based on 100 parts by weight of the resin composition.

When the setting polymers are produced by copolymerization according to the present invention, such monomers as having functional groups which become active with the initiators being used in synthesis of the setting polymers are used. For example, styrene derivatives are preferred for polymerization of the styryl groups with anionic polymerization initiators, while N-phenylmaleimide derivatives are preferred for polymerization of the maleimide groups. One may select any monomers suitable to achieve the end properties. For improvement of the flexibility of the cured products, styrene is used; for lower dielectric constant and improvement of the surface lubricity of the cured products, fluorinated monomers such as o-fluorostyrene, m-fluorostyrene, p-fluorostyrene and 2,3,4,5,6-pentafluorostyrene are used; for imparting flame retarding property, brominated monomers such as obromostyrene, m-bromostyrene, p-bromo styrene and 2,3,4,5,6-pentafluorostyrene are used; for improvement of sulubility and adherence with metals, high polarity monomers such as o-vinylpyridine, m-vinylpyridine and p-vinylpyridine are used. The ratio of the multi-functional compounds to the monomers to be copolymerized is not critical, but may be in the range of 5:95 to 95:5 to balance requisite characteristics. Since an increased proportion of the monomers to be incorporated causes a reduction in the number of cross linking points with the the multi-functional compounds, most preferably the ratio should be in the range of 40:60 to 95:5. A combination of two or more of the monomers may be used.

Cross linking aids to be used in the present invention include bismaleimide compounds such as bis(4-maleimidephenyl)methane, 2,2-bis[4-(4-maleimidephenoxy) phenyl) propane, 2,2-bis[4-(4-maleimidephenoxy)phenyl)-1,1,1,3,3,3-hexafloropropane and 2,2-bis[4-(2-trifluoromethyl-4-maleimidephenoxy)phenyl)-1,1,1,3,3,3 -hexafloropropane, divinyl compounds such as divinyl benzene and bis(4-vinylphenyl)methane, multi-functional acrylate compounds such as ethylene glycol diacrylate, diethylene glycol diacrylate, glycerin triacrylate and pentaerythritol triacrylate, and polymers such as poly(vinylacrylate), poly(4-acryloyloxystyrene) and the like having acryl groups in side chains. Particularly, in case the cured products are attained under irradiation, the multi-functional acrylate compounds acting as cross linking agents, compounds having acryl groups in side chains should be employed.

Optically functional initiators to be used are optically radical generating agents such as bezophenone, benzoin, dibenzylether and the like. Radiation lights for curing reaction include ultraviolet radiation and visible lights, with preferred ones being ultraviolet radiation, especially the i ray (436 nm) and the g ray (365 nm) from a high pressure mercury lamp.

The present resin composition can form a resin film from either a solvent system or a non-solvent system. Solvents for preparation of a varnish in the solvent system include, for example, toluene, xylene, benzene, hexafluorobenzene, acetone, methylethylketone, N,N-dimethylformamide, N-methylpyrrolidone, dimethylsulfoxide, trichloroethylene, trichloroethane, dichloromethane, dioxane and ethyl acetate. Any solvents may be used so long as they can dissolve uniformly the composition.

Since the multi-functional compounds having functional groups different in reactivity from each other are polymerized using an initiator which is active for one of the functional groups without causing any reaction with the other functional groups, there can be produced a polymer having unreacted functional groups in side chains. Moreover, a mono-functional monomer which is reactive with a polymerization initiator used may be copolymerized to impart various properties to the resultant setting polymer. The copolymer unlike blend does not raise any problem of phase separation and the like, permitting a uniform cured product to be readily produced.

DESCRIPTION OF PREFERRED EMBODIMENTS

The present invention will be practically illustrated with reference to the following Examples without being limited thereto.

EXAMPLE 1

Synthesis of (4-maleimidephenyl)(4-styryl)ether 50 gram of 4-bromostyrene and 38 gram of p-aminophenol were reacted in dioxane in the presence of potassium hydroxide as catalyst to synthesize (4-maleimidephenyl) (4-styryl)ether. 80 gram of the product was refined by recrystallization, and thereafter, dissolved in diethylether, added dropwise with 37 gram of maleic anhydride at room temperature over about one hour, and reacted for two hours. The precipitated product was removed by suction filter, transferred into a flask containing acetic anhydride and anhydrous sodium acetate, reacted at 90° C. for about two hours, and further reacted at room temperature for one hour, and thereafter, the reaction solution was poured into a cold water to produce a precipitate which was suction filtered. The resultant rough product was washed with water and hexane, and recrystallized from benzene. The yield of the product was 90 gram.

The product had a melting point of 95°–98° C. and exhibited with $^1$H-NMR the peaks at 6.8 ppm (vinylene group), 5.3 and 5.8 ppm (vinyl group), and at about 7 ppm (phenylene) establishing that (4-maleimidephenyl) (4-styryl)ether was synthesized.

To the synthesized monomer, there was added an anionic polymerization initiator, potassium t-butoxide in a ratio thereof to the monomer of 1:50, and the resultant mixture was reacted in tetrahydrofuran at zero centigrade for 3 hours. The yield of the polymer was about 70%. Determination of the structure of the product with $^1$H-NMR indicated that the peak at 6.8 ppm due to the vinylene of the maleimide group disappeared and instead a new peak was observed at about 4 ppm. The peaks at 5.3 and 5.8 ppm due to the vinyl group remained unchanged. It could be confirmed, therefore, that only the maleimide group in the monomer was addition-polymerized to produce the polymer.

The produced polymer was shaped in a metallic mold with a spacer of a thickness of 2 mm to produce a resin plate. The curing conditions consisted of heat-treatments for 40 minutes at 130° C. and for 2 hours at an evaluated temperature of 170° C. under a pressure. The resultant resin plate was evaluated for characteristics. The dielectric constant of samples was calculated using measurements of electrostatic capacity according to JIS-C-6481 with LF impedance analyzer 4192A available from Hewlett Packard Co. Samples of the dimentions of 7 mm×7 mm were cut out from the resin plate and determined for the thermal expansion coefficient (50 to 220° C.) in the thickness direction with TM-3000, an apparatus for measuring thermomechanical properties available from SHINKU RIKO. The measurement was made at a rate of increasing temperature of 2° C./min. in a compression mode under a load of 10 gram. The flexural strength was determined by means of AUTOGRAPH DDS-5000 available from SHIMAZU SEISAKUSHO according to JIS-C-6481. Samples of the dimentions of 50 mm×5 mm were cut out from the resin plate and determined for the flexural strength under the conditions of a distance between supporting points of 30 mm and a bending rate of 2 mm/min. The thermal decomposition onset temperature was determined using TGD-7000 RH, a high speed differential thermal analyzer available from SHINKU RIKO. 10 gram of a powdery sample obtained by grinding the resin were determined for the thermal decomposition onset temperature by plotting a weight loss under heating in an atmosphere of helium flowing at a rate of 100 cm$^3$/min. and at a rate of increasing temperature of 5° C./min. assuming that the temperature at a weight loss of 5% corresponded the thermal decomposition onset temperature. The results are summarized in Table.

EXAMPLE 2

To a (4-maleimidephenyl) (4-styryl) ether synthesized in the same procedure as in Example 1 used as monomer, there was added a cationic polymerization initiator, boron trifluoride diethyl ether in a ratio thereof to the monomer of 1:50, and the resultant mixture was reacted in dichloromethane at zero centigrade for 3 hours. The yield of the polymer was about 30%. Determination of the structure of the product with $^1$H-NMR indicated that the peaks at 5.3 and 5.8 ppm due to the vinyl group disappeared and instead a new peak was observed at about 1.5 ppm. The vinylene peak of the maleimide group at 6.8 ppm remained unchanged. It could be confirmed, therefore, that only the vinyl group in the monomer was addition-polymerized to produce the polymer.

The produced polymer was shaped in a metallic mold with a spacer of a thickness of 2 mm to produce a resin plate in the same manner as in Example 1. The curing conditions consisted of heat-treatments for 40 minutes at 130° C. and for 2 hours at an elevated temperature of 170° C. under a pressure. The resultant resin plate was evaluated for characteristics. The measurement results were summarized in Table.

EXAMPLE 3

To a methylene (4-maleimidephenyl) (4-styryloxy) synthesized from p-hydroxystyrene and 4-aminobenzo bromide in the same procedure as in Example 1 used as monomer, there was added an anionic polymerization initiator, potassium t-butoxide in a ratio thereof to the monomer of 1:50 in an atmosphere of nitrogen, and the resultant mixture was reacted in tetrahydrofuran at zero centigrade for 3 hours. The yield of the polymer was about 70%. Determination of the structure of the product with $^1$H-NMR indicated that the peak at 6.8 ppm due to the vinylene of the maleimide group disappeared and instead a new peak was observed at about 4 ppm. The peaks at 5.3 and 5.8 ppm due to the vinyl group remained unchanged. It could be confirmed, therefore, that only the maleimide group in the monomer was addition-polymerized to produce the polymer.

The produced polymer was shaped in a metallic mold with a spacer of a thickness of 2 mm to produce a resin plate in the same manner as in Example 1. The curing conditions consisted of heat-treatments for 40 minutes at 130° C. and for 2 hours at an elevated temperature of 170° C. under a pressure. The resultant resin plate was evaluated for characteristics. The measurement results are summarized in Table. The results for Example and Comparative Example are shown in the Table.

EXAMPLE 4

To a methylene (4-maleimidephenyl) (4-styryloxy) synthesized in the same procedure as in Example 3 used as monomer, there was added a cationic polymerization initiator, boron trifluoride diethyl ether in a ratio thereof to the monomer of 1:50, and the resultant mixture was reacted in dichloromethane at zero centigrade for 3 hours. The yield of the polymer was about 30%. Determination of the structure of the product with $^1$H-NMR indicated that the peaks at 5.3 and 5.8 ppm due to the vinyl group disappeared and instead a new peak was observed at about 1.5 ppm. The vinylene peak of the maleimide group at 6.8 ppm remained unchanged. It could be confirmed, therefore, that only the vinyl group in the monomer was addition-polymerized to produce the polymer.

The produced polymer was shaped in a metallic mold with a spacer having a thickness of 2 mm to produce a resin plate in the same manner as in Example 1. The curing conditions consisted of heat-treatments for 40 minutes at 130° C. and for 2 hours at an elevated temperature of 170° C. under a pressure. The resultant resin plate was evaluated for characteristics. The measurement results were summarized in Table.

EXAMPLE 5

To a methylene(4-maleimidephenylmethylene) vinylether synthesized from hydroxyethylene and 4-aminobenzo bromide in the same procedure as in Example 1 used as monomer, there was added an anionic polymerization initiator, potassium t-butoxide in a ratio thereof to the monomer of 1:50 in an atmosphere of nitrogen, and the resultant mixture was reacted in tetrahydrofuran at zero centigrade for 3 hours. The yield of the polymer was about 70%. Determination of the structure of the product with $^1$H-NMR indicated that the peak at 6.8 ppm due to the vinylene of the maleimide group disappeared and instead a new peak was observed at about 4 ppm, The peaks at 5.3 and 5.8 ppm due to the vinyl group remained unchanged. It could be confirmed, therefore, that only the maleimide group in the monomer was addition-polymerized to produce the polymer.

The produced polymer was shaped in a metallic mold with a spacer of a thickness of 2 mm to produce a resin plate in the same manner as in Example 1. The curing conditions consisted of heat-treatments for 40 minutes at 130° C. and for 2 hours at an elevated temperature of 170° C. under a pressure. The resultant resin plate was evaluated for characteristics. The measurement results are summarized in Table. The results for Example and Comparative Example are shown in the Table.

EXAMPLE 6

To a methylene(4-maleimidephenylmethylene) vinylether synthesized in the same procedure as in Example 5 used as monomer, there was added a cationic polymerization initiator, boron trifluoride diethyl ether in a ratio thereof to the monomer of 1:50, and the resultant mixture was reacted in dichloromethane at zero centigrade for 3 hours. The yield of the polymer was about 30%. Determination o the structure of the product with $^1$H-NMR indicated that the peaks at 5.3 and 5.8 ppm due to the vinyl group disappeared and instead a new peak was observed at about 1.5 ppm. The vinylene peak of the maleimide group at 6.8 ppm remained unchanged. It could be confirmed, therefore, that only the vinyl group in the monomer was addition-polymerized to produce the polymer.

The produced polymer was shaped in a metallic mold with a spacer having a thickness of 2 mm to produce a resin plate in the same manner as in Example 1. The curing conditions consisted of heat-treatments for 40 minutes at 130° C. and for 2 hours at an elevated temperature of 170° C. under a pressure. The resultant resin plate was evaluated for characteristics. The measurement results were summarized in Table.

EXAMPLE 7

To a methylene(4-maleimidephenylmethylene) vinylether synthesized from hydroxyethylene and 4-vinylbenzo bromide in the same procedure as in Example 1 used as monomer, there was added an anionic polymerization initiator, n-butyl lithium in a ratio thereof to the monomer of 1:50 in an atmosphere of nitrogen, and the resultant mixture was reacted in tetrahydrofuran at zero centigrade for 3 hours. The yield of the polymer was about 70%. Determination of the structure of the product with $^1$H-NMR indicated that the peak at 6.8 ppm due to the vinylene of the maleimide group disappeared and instead a new peak was observed at about 4 ppm. The peaks at 5.3 and 5.8 ppm due to the vinyl group remained unchanged. It could be confirmed, therefore, that only the maleimide group in the monomer was addition-polymerized to produce the polymer.

The produced polymer was shaped in a metallic mold with a spacer of a thickness of 2 mm to produce a resin plate in the same manner as in Example 1. The curing conditions consisted of heat-treatments for 40 minutes at 30° C. and for 2 hours at an elevated temperature of 170° C. under a pressure. The resultant resin plate was evaluated for characteristics. The measurement results are summarized in Table. The results for Example and Comparative Example are shown in the Table.

EXAMPLE 8

To a methylene(4-maleimidephenylmethylene) vinylether synthesized in the same procedure as in Example 7 used as monomer, there was added a cationic polymerization initiator, boron trifluoride diethyl ether in a ratio thereof to the monomer of 1:50, and the resultant mixture was reacted in dichloromethane at zero centigrade for 3 hours. The yield of the polymer was about 30%. Determination of the structure of the product with $^1$H-NMR indicated that the peaks at 5.3 and 5.8 ppm due to the vinyl group disappeared and instead a new peak was observed at about 1.5 ppm. The vinylene peak of the maleimide group at 6.8 ppm remained unchanged. It could be confirmed, therefore, that only the vinyl group in the monomer was addition-polymerized to produce the polymer.

The produced polymer was shaped in a metallic mold with a spacer having a thickness of 2 mm to produce a resin plate in the same manner as in Example 1. The curing conditions consisted of heat-treatments for 40 minutes at 130° C. and for 2 hours at an elevated temperature of 170° C. under a pressure. The resultant resin plate was evaluated for characteristics. The measurement results were summarized in Table.

EXAMPLE 9

To a N-(4-vinyltolyl)maleimide synthesized from amino(4-styryl)methylene in the same procedure as in Example 1 used as monomer, there was added an anionic polymerization initiator, potassium t-butoxide in a ratio thereof to the monomer of 1:50 in an atmosphere of nitrogen, and the resultant mixture was reacted in tetrahydrofuran at zero centigrade for 3 hours. The yield of the polymer was about 70%. Determination of the structure of the product with $^1$H-NMR indicated that the peak at 6.8 ppm due to the vinylene of the maleimide group disappeared and instead a new peak was observed at about 4 ppm. The peaks at 5.3 and 5.8 ppm due to the vinyl group remained unchanged. It could be confirmed, therefore, that only the maleimide group in the monomer was addition-polymerized to produce the polymer.

The produced polymer was shaped in a metallic mold with a spacer of a thickness of 2 mm to produce a resin plate in the same manner as in Example 1. The curing conditions consisted of heat-treatments for 40 minutes at 30° C. and then an elevation of temperature to 170° C.

Copolymerization of a multi-functional monomer and a mono-functional monomer will be illustrated hereunder.

EXAMPLE 10

50 parts by weight of a (4-maleimidephenyl)(4-styryl)ether synthesized in the same procedure as in Example 1 and 50 parts by weight of styrene were used as monomers, to which a cationic polymerization initiator, boron trifluoride diethyl ether was added in a ratio thereof to the monomers of 1:50, and the resultant mixture was reacted in dichloromethane at zero centigrade for 3 hours. The yield of the polymer was about 30%. Determination of the structure of the product with $^1$H-NMR indicated that the peaks at 5.3 and 5.8 ppm due to the vinyl group of the multi-functional monomer disappeared and instead a new peak was observed at about 1.5 ppm. The peak at 6.8 ppm due to the vinylene of the maleimide group remained unchanged. It could be confirmed, therefore, that only the vinyl group in the monomer was addition-polymerized to produce the polymer.

The produced polymer was shaped in a metallic mold with a spacer having a thickness of 2 mm to produce a resin plate in the same manner as in Example 1. The curing conditions consisted of heat-treatments for 40 minutes at 130° C. and for 2 hours at an elevated temperature of 170° C. under a pressure. The resultant resin plate was evaluated for characteristics. The measurement results were summarized in Table. The results of Example and Comparative Example are shown in the Table.

EXAMPLE 11

50 parts by weight of a (4-maleimidephenyl)(4-styryl)ether synthesized in the same procedure as in Example 1 and 50 parts by weight of N-(pentafluorophenyl)maleimide were used as monomers, to which an anionic polymerization initiator, potassium t-butoxide was added in a ratio thereof to the monomers of 1:50 in an atmosphere of nitrogen, and the resultant mixture was reacted in tetrahydrofuran at zero centigrade for 3 hours. The yield of the polymer was about 70%. Determination of the structure of the product with $^1$H-NMR indicated that the peak at 6.8 ppm due to the vinylene of the maleimide group of the multi-functional monomer disappeared and instead a new peak was observed at about 4 ppm. The peaks at 5.3 and 5.8 ppm due to the vinyl group remained unchanged. It could be confirmed, therefore, that only the maleimide group in the monomer was addition-polymerized to produce the polymer.

The produced polymer was shaped in a metallic mold with a spacer having a thickness of 2 mm to produce a resin plate in the same manner as in Example 1. The curing conditions consisted of heat-treatments for 40 minutes at 130° C. and for 2 hours at an elevated temperature of 170° C. under a pressure. The resultant resin plate was evaluated for characteristics. The measurement results were summarized in Table. The results of Example and Comparative Example are shown in the Table.

EXAMPLE 12

50 parts by weight of a (4-maleimidephenyl)(4-styryl)ether synthesized in the same procedure as in Example 1 and 50 parts by weight of p-vinylpyridine were used as monomers, to which a cationic polymerization initiator, boron trifluoride diethyl ether was added in a ratio thereof to the monomers of 1:50, and the resultant mixture was reacted in dichloromethane at zero centigrade for 3 hours. The yield of the polymer was about 30%. Determination of the structure of the product with $^1$H-NMR indicated that the peaks at 5.3 and 5.8 ppm due to the vinyl group of the multi-functional monomer disappeared and instead a new peak was observed at about 1.5 ppm. The peak at 6.8 ppm due to the vinylene of the maleimide group remained unchanged. It could be confirmed, therefore, that only the vinyl group in the monomer was addition-polymerized to produce the polymer.

The produced polymer was shaped in a metallic mold with a spacer having a thickness of 2 mm to produce a resin plate in the same manner as in Example 1. The curing conditions consisted of heat-treatments for 40 minutes at 130° C. and for 2 hours at an elevated temperature of 170° C. under a pressure. The resultant resin plate was evaluated for characteristics. The measurement results were summarized in Table. The results of Example and Comparative Example are shown in the Table.

COMPARATIVE EXAMPLE 3

60 parts by weight of 4-methyl-2,4-bis(p-N-maleimidephenyl)-1-penten as disclosed in Japanese Patent Publication No. Hei 3-43287 and 40 parts by weight of N,N'-4,7-dioxadecane-1,10-bismaleimide were mixed and shaped in a metallic mold with a spacer having a thickness of 2 mm to produce a resin plate in the same manner as in Example 1. The curing conditions consisted of heat-treatments for 3 hours at 130° C. for 2 hours at an elevated temperature of 200° C. and for 2 hours at a further elevated temperature of 250° C. under a pressure. The resultant resin plate was evaluated for characteristics. The measurement results were summarized in Table.

The results of Examples and Comparative Examples are shown in the Table.

TABLE 1

| | Dielectric constant | Thermal expansion coefficient × $10^5$ ($K_d^{-1}$) | Glass transition temperature (°C.) | Flexural strength ($MN/m^2$) | Thermal decomposition onset temperature (°C.) |
|---|---|---|---|---|---|
| Example 1 | 3.6 | 7.2 | 300 | 12.5 | 425 |
| Example 2 | 3.6 | 7.0 | 300 | 13.0 | 410 |
| Example 3 | 3.8 | 7.2 | 290 | 13.5 | 430 |
| Example 4 | 3.7 | 7.5 | 320 | 13.0 | 430 |
| Example 5 | 3.6 | 7.6 | 300 | 12.5 | 425 |
| Example 6 | 3.6 | 7.4 | 310 | 13.5 | 425 |
| Example 7 | 3.6 | 7.5 | 300 | 14.0 | 425 |
| Example 8 | 3.6 | 7.6 | 310 | 13.0 | 425 |
| Example 9 | 3.6 | 7.7 | 300 | 13.0 | 425 |
| Example 10 | 3.6 | 7.5 | 300 | 13.5 | 425 |
| Example 11 | 3.1 | 8.1 | 385 | 11.5 | 425 |
| Example 12 | 2.8 | 8.5 | 280 | 12.0 | 430 |
| Comparative Example 1* | — | — | — | — | — |
| Comparative Example 2* | — | — | — | — | — |
| Comparative Example 3 | 3.8 | 9.1 | 265 | 9.5 | 425 |

*It was impossible to shape any resin plate for evaluation of characteristics.

The multi-functional monomer according to the present invention allows the synthesis of a setting polymer having a reactive functional group in a side chain by a polymerization process in one step reaction using a specific initiator which is selected depending upon the reactivities of the functional groups of the monomer. Moreover, the multi-functional monomer may be copolymerized with other monomers such as fluorinated monomers, polar monomers and the like to impart requisite electrical and mechanical properties to the resultant polymer. Particularly, the use of the monomer having a maleimide group gives rise to an excellent thermal durability, and the setting polymer obtained from copolymerization of such monomer with the fluorinated monomer can provide a cured product having excellent electrical properties and mechanical properties such as flexural strength and the like. The cured products are considered applicable as insulating materials having excellent thermal durability and a lower dielectric constant.

What is claimed is:

1. A polymerizable compound represented by the general formula (4):

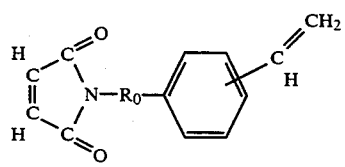

where $R_0$ is a divalent organic group having 6 to 20 carbon atoms and containing a phenylene group.

2. A polymerizable compound represented by the general formula:

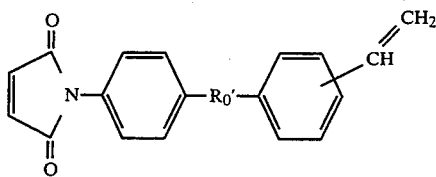

wherein $R_0'$ represents a divalent group selected from the group consisting of —O—, —S—, —O—CO—, —CO—O—, —CH$_2$O— and —O—CH$_2$—.

3. A compound according to claim 1, wherein the compound is

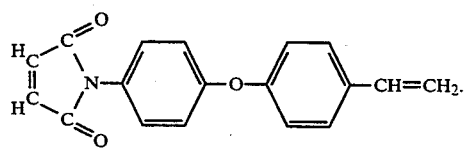

4. A compound according to claim 1, wherein the compound is

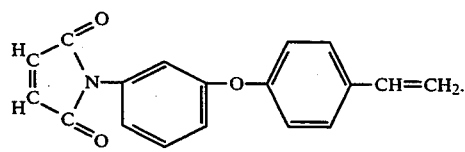

5. A compound according to claim 1, wherein the compound is

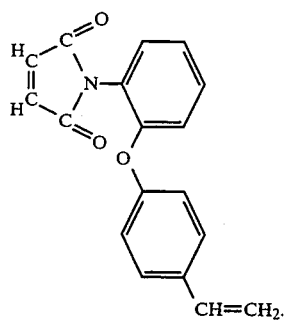

6. A compound according to claim 1, wherein the compound is

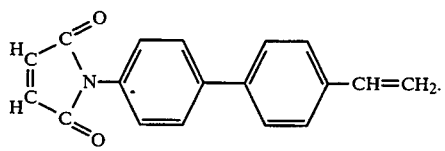

7. A compound according to claim 1, wherein the compound is

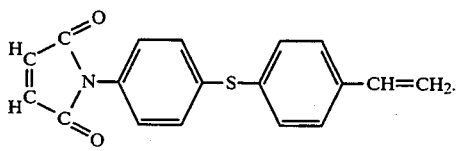

8. A compound according to claim 1, wherein the compound is

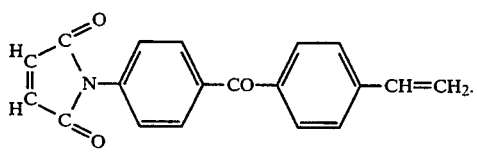

9. A compound according to claim 1, wherein the compound is

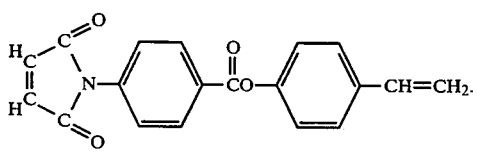

10. A compound according to claim 1, wherein the compound is

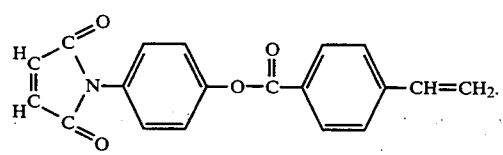

11. A compound according to claim 1, wherein the compound is

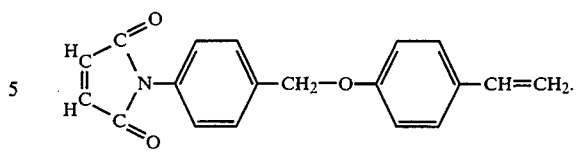

12. A compound according to claim 1, wherein the compound is

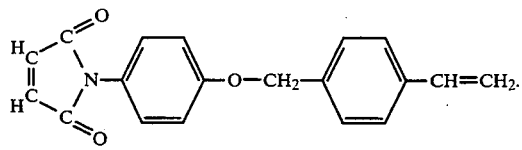

13. A compound according to claim 1, wherein the compound is

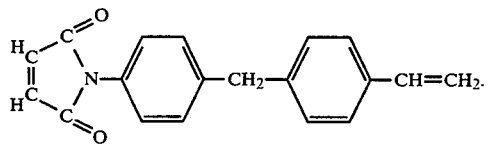

14. A compound according to claim 1, wherein the compound is

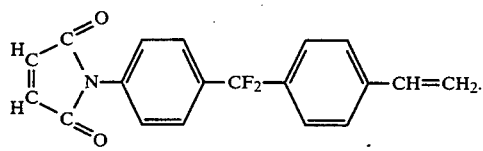

15. A compound according to claim 1, wherein the compound is

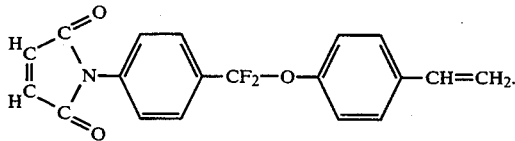

16. A compound according to claim 1, wherein the compound is

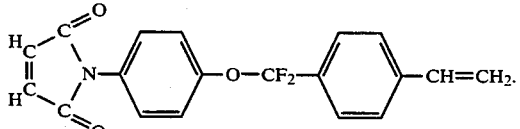

17. A compound according to claim 1, wherein the compound is

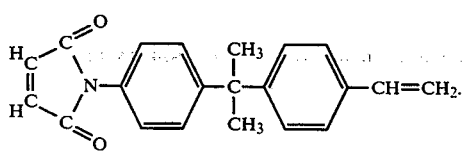

18. A compound according to claim 1, wherein the compound is

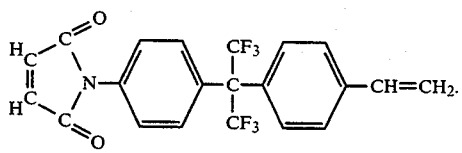

19. A compound according to claim 1, wherein the compound is

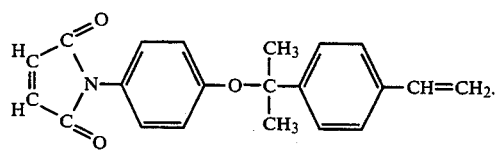

20. A compound according to claim 1, wherein the compound is

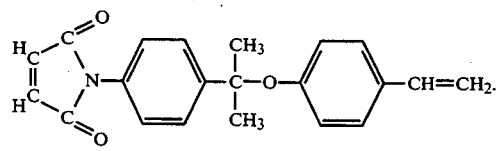

21. A compound according to claim 1, wherein the compound is

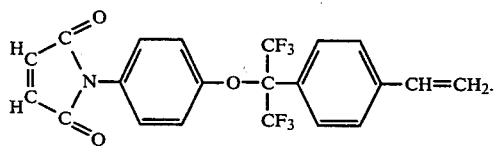

22. A compound according to claim 1, wherein the compound is

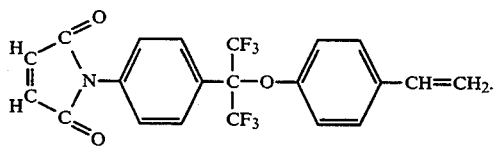

23. A compound according to claim 1, wherein the compound is

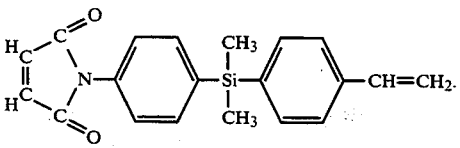

24. A compound according to claim 1, wherein the compound is

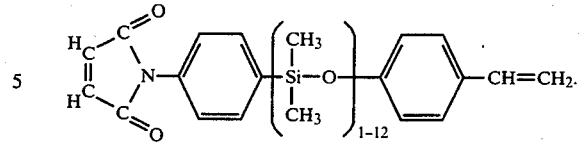

25. A compound according to claim 1, wherein the compound is

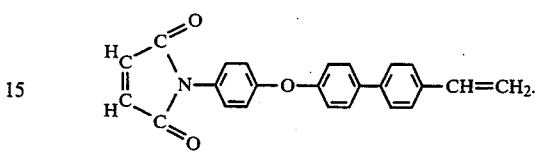

26. A compound according to claim 1, wherein the compound is

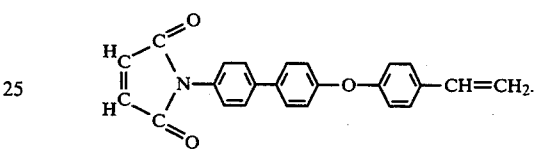

27. A compound according to claim 1, wherein the compound is

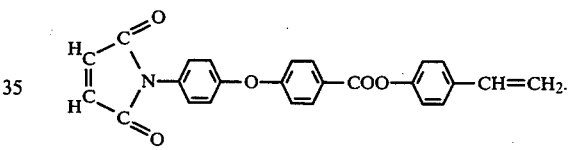

28. A compound according to claim 1, wherein the compound is

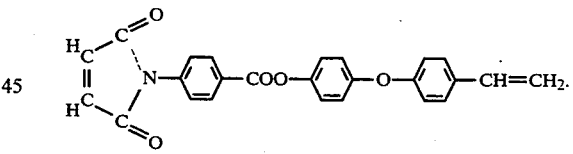

29. A compound according to claim 1, wherein the compound is

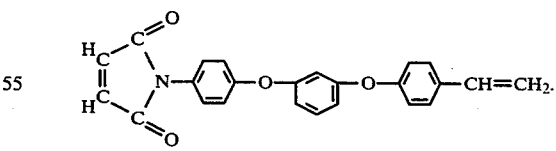

30. A compound according to claim 1, wherein the compound is

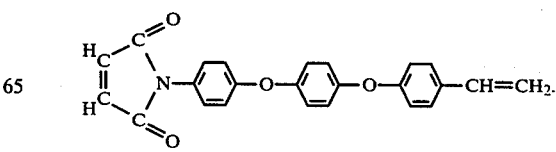

31. A compound according to claim 1, wherein the compound is
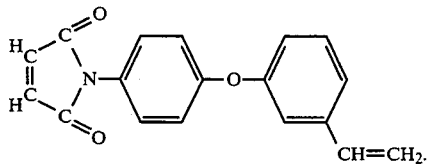
32. A compound according to claim 1, wherein the compound is
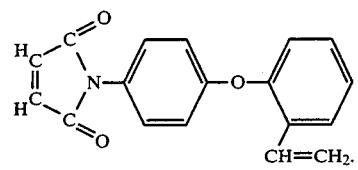
33. A compound according to claim 1, wherein the compound is
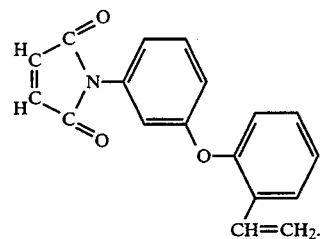
* * * * *